US012194281B2

(12) United States Patent
Okihara

(10) Patent No.: US 12,194,281 B2
(45) Date of Patent: Jan. 14, 2025

(54) SYRINGE, SYRINGE ASSEMBLY, AND MANUFACTURING METHOD OF SYRINGE

(71) Applicant: TERUMO KABUSHIKI KAISHA, Tokyo (JP)

(72) Inventor: Hitoshi Okihara, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 1142 days.

(21) Appl. No.: 17/038,845

(22) Filed: Sep. 30, 2020

(65) Prior Publication Data

US 2021/0008285 A1  Jan. 14, 2021

Related U.S. Application Data

(63) Continuation of application No. PCT/JP2019/013236, filed on Mar. 27, 2019.

(30) Foreign Application Priority Data

Mar. 30, 2018 (JP) .................................. 2018-066367

(51) Int. Cl.
A61M 5/31 (2006.01)
A61M 5/32 (2006.01)

(52) U.S. Cl.
CPC ... A61M 5/3129 (2013.01); *A61M 2005/3131* (2013.01); *A61M 5/3202* (2013.01); *A61M 2207/00* (2013.01)

(58) Field of Classification Search
CPC .............. A61M 5/3129; A61M 5/3202; A61M 2005/3131; A61M 2207/00; A61M 5/002; A61M 5/31513; A61M 2005/31521
See application file for complete search history.

(56) References Cited

U.S. PATENT DOCUMENTS 7,144,389 B2   12/2006 Ferguson et al.
2007/0129676 A1*  6/2007 Lin ..................... A61M 5/322
                                                           604/110
(Continued)

FOREIGN PATENT DOCUMENTS

JP   2007117272 A   5/2007
JP   2013132349 A   7/2013
(Continued)

OTHER PUBLICATIONS

International Search Report (with English Translation) and Written Opinion issued in corresponding International Patent Application No. PCT/JP2019/013236, 6 pages (Jun. 4, 2019).

(Continued)

*Primary Examiner* — Lauren P Farrar
(74) *Attorney, Agent, or Firm* — Buchanan Ingersoll & Rooney PC

(57) ABSTRACT

A syringe of a syringe assembly is provided with a body portion capable of being filled with a drug solution and a female port nozzle portion which extends from a distal end of the body portion and includes a communication port on a proximal end of the female port nozzle. The body portion includes a distal end wall surface and a side wall surface to which a liquid lubricant is applied. The distal end wall surface includes a concave portion arranged radially outside an inner edge portion adjacent to the communication port and concave in a distal end direction more than at least a part of the inner edge portion, and the concave portion is arranged to fully surround the communication port and may store the liquid lubricant.

20 Claims, 14 Drawing Sheets

(56) References Cited

U.S. PATENT DOCUMENTS

| | | |
|---|---|---|
| 2013/0165853 A1 | 6/2013 | Kawamura |
| 2015/0018800 A1* | 1/2015 | Reb .................. A61B 17/12186 |
| | | 604/230 |
| 2015/0174338 A1 | 6/2015 | Takemoto |
| 2016/0166760 A1* | 6/2016 | Orofino ................. A61J 1/2096 |
| | | 604/416 |
| 2018/0264198 A1 | 9/2018 | Okihara |
| 2018/0333539 A1* | 11/2018 | Ku ...................... A61M 5/3221 |

FOREIGN PATENT DOCUMENTS

| | | |
|---|---|---|
| WO | 2014141471 A1 | 9/2014 |
| WO | 2017/086366 A1 | 5/2017 |

OTHER PUBLICATIONS

Office Action (Examination Report) issued Dec. 15, 2021, by the Patent Office, Government of India, in corresponding India Patent Application No. 202017041453 with an English Translation of the Office Action. (6 pages).

The extended European Search Report issued Apr. 15, 2021, by the European Patent Office in corresponding European Patent Application No. 19775174.6-1122. (5 pages).

\* cited by examiner

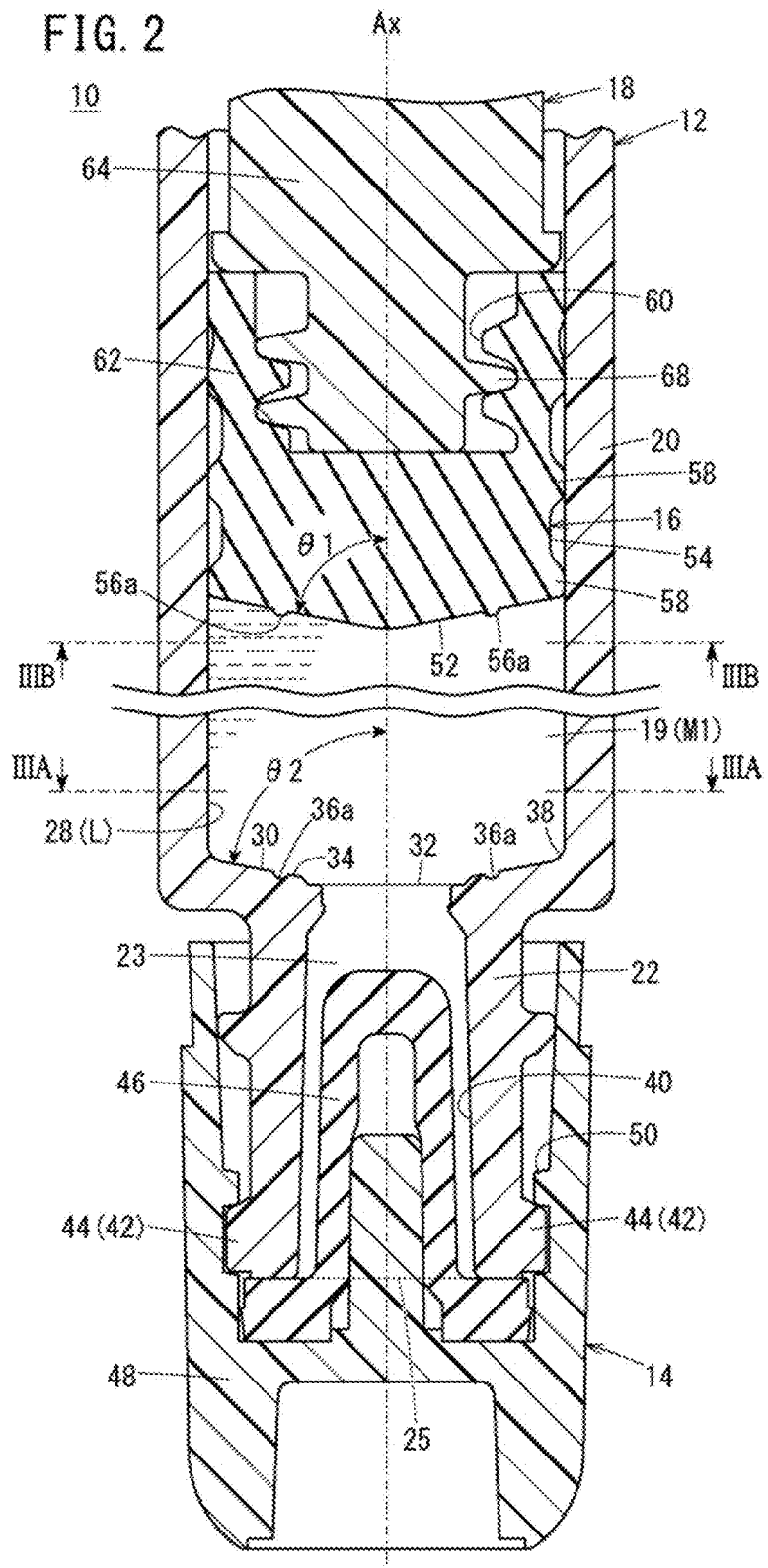

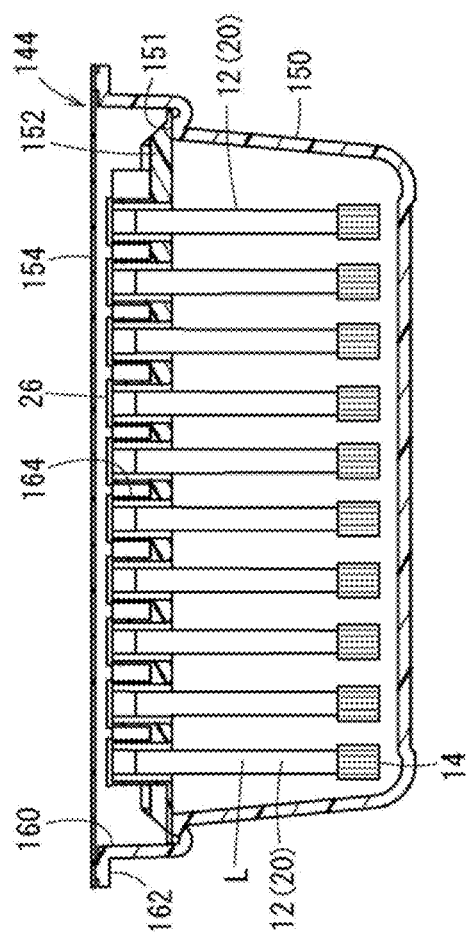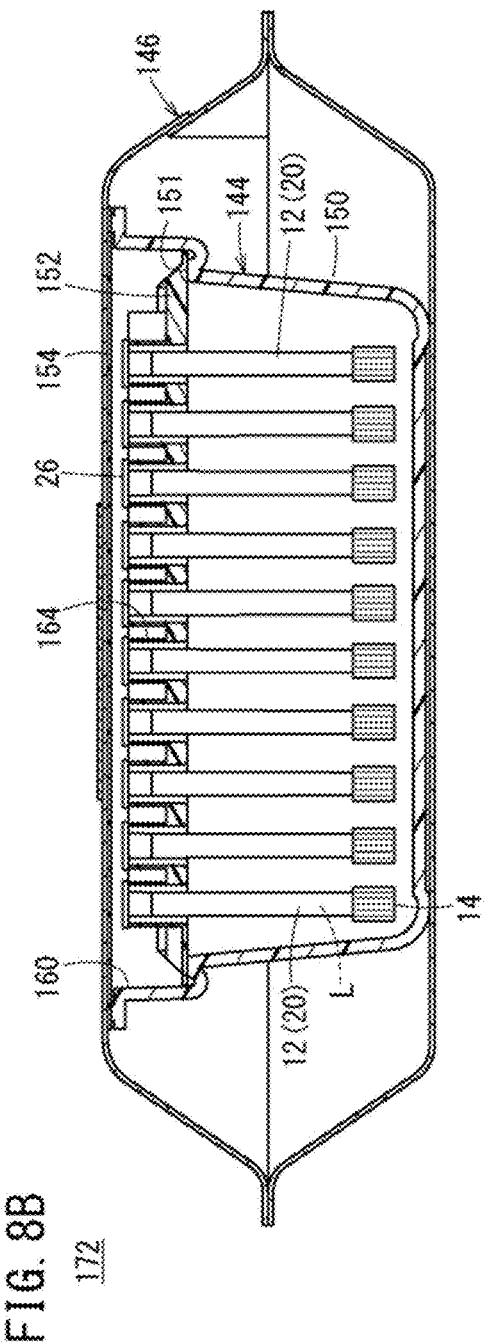

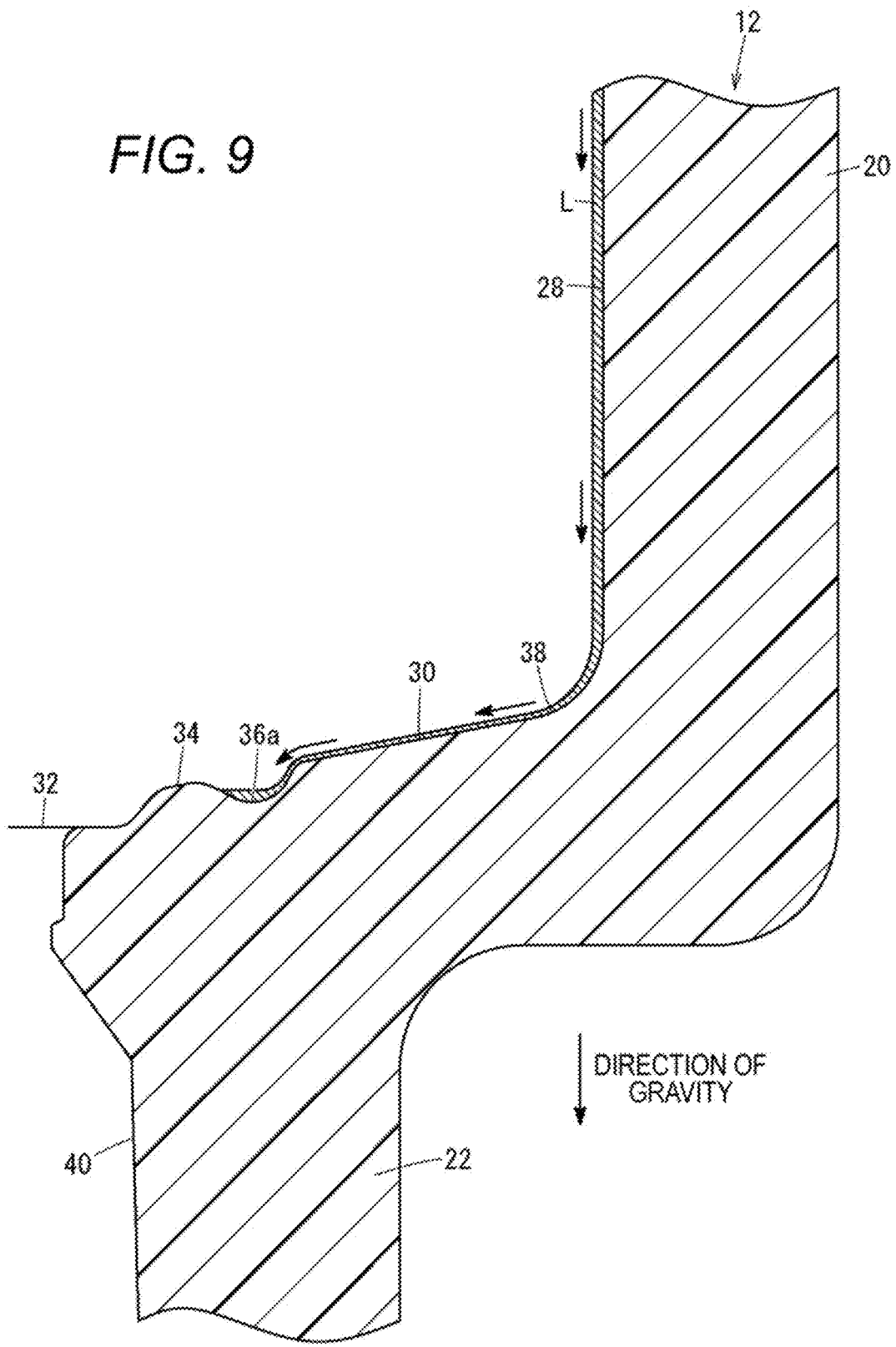

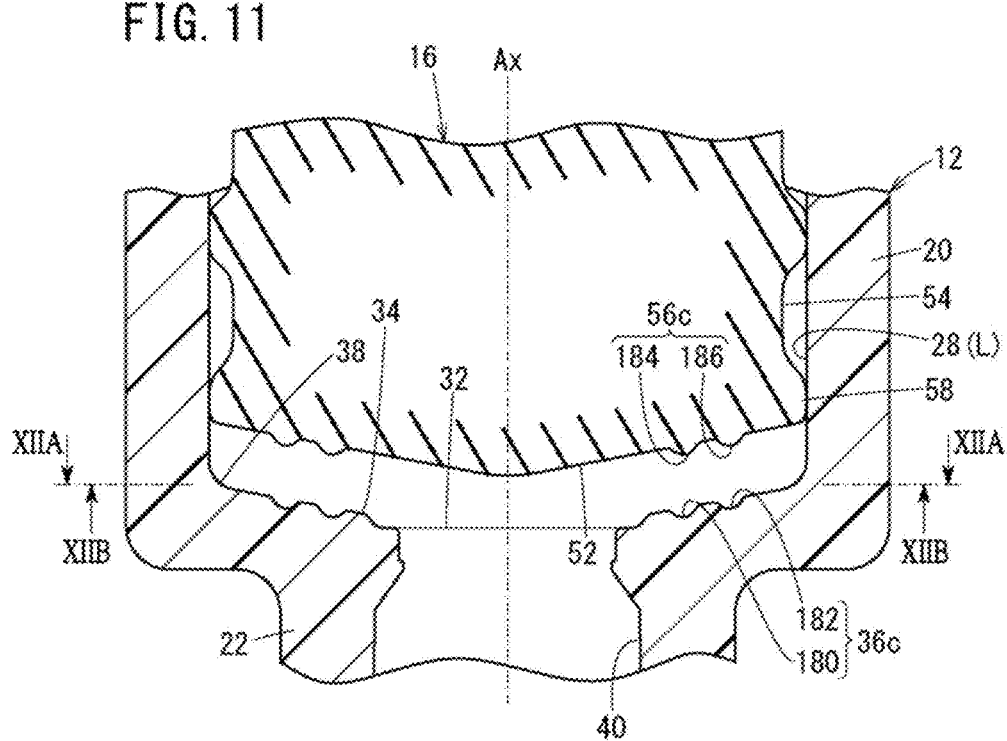

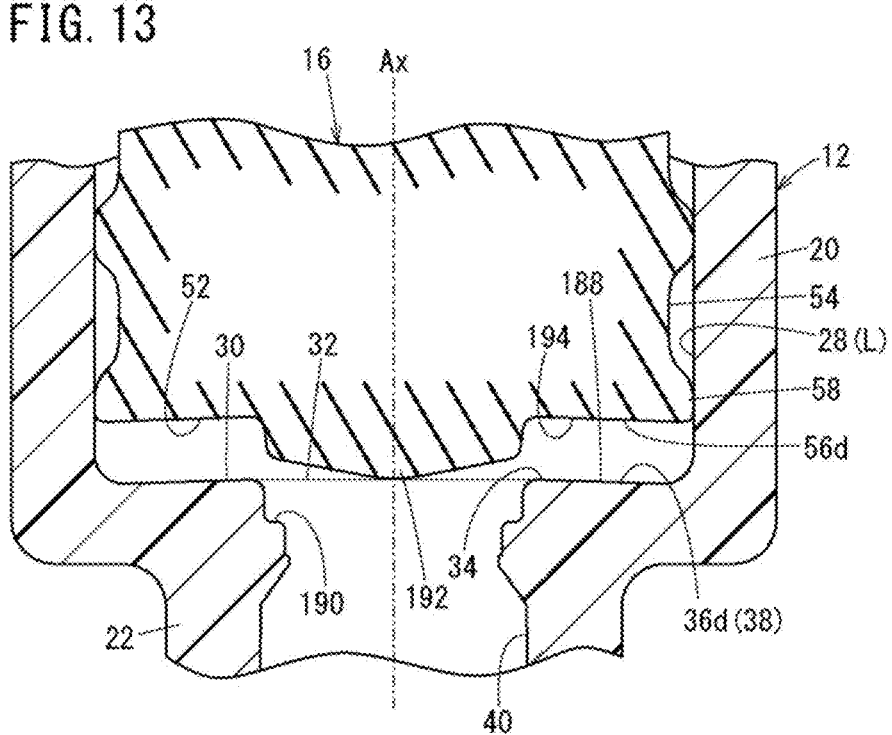

SYRINGE, SYRINGE ASSEMBLY, AND MANUFACTURING METHOD OF SYRINGE

CROSS-REFERENCES TO RELATED APPLICATIONS

This application is a continuation of International Application No. PCT/JP2019/013236 filed on Mar. 27, 2019, which claims priority to Japanese Application No. 2018-066367 filed on Mar. 30, 2018, the entire content of both of which is incorporated herein by reference.

FIELD OF THE INVENTION

The present disclosure generally relates to a syringe, a syringe assembly, and a manufacturing method of a syringe.

BACKGROUND DISCUSSION

For example, Japanese Patent Application Publication No. 2013-132349 A discloses a syringe provided with a body portion including an inner cavity capable of being filled with a drug solution, a female port nozzle portion which extends from a distal end of the body portion into which a male port nozzle portion being a male luer is inserted, and a proximal end opening formed on a proximal end portion of the body portion. By inserting a gasket into the body portion of such syringe in a state in which liquid lubricant such as silicone oil is applied to a side wall surface (inner peripheral surface) of the body portion, a syringe assembly is formed.

During a process of manufacturing, storing, and transporting the syringe assembly, the syringe may be held for a relatively long period of time in a state in which the syringe is set up such that a distal end of the female port nozzle portion faces downward. In such a state in the distal end of the female port nozzle is facing downward, the liquid lubricant applied to the inner peripheral surface of the syringe (gasket sliding surface of the syringe) might drip due to gravity and adhere to the inner peripheral surface of the female port nozzle portion. When the liquid lubricant adheres to the inner peripheral surface of the female port nozzle portion, connection strength of connection between the female port nozzle portion (female luer) and the male port nozzle portion (male luer) (luer taper connection) decreases, causing a reduction in liquid tightness or transfer of the liquid lubricant to the male port nozzle portion, so that there is a possibility that the male port nozzle portion and another device (for example, an injection needle) cannot be connected properly.

SUMMARY

A syringe, a syringe assembly, and a manufacturing method of a syringe are disclosed, which are capable of suppressing the liquid lubricant from adhering to the inner peripheral surface of the female port nozzle portion and securing prevention of the connection strength of the luer taper connection from lowering and prevention of the liquid lubricant from transferring to the male port nozzle portion.

In accordance with an aspect, a syringe is disclosed, which includes a body portion including an inner cavity configured to be filled with a drug solution, a female port nozzle portion that extends from a distal end of the body portion into which a male luer is inserted, and a proximal end opening formed on a proximal end portion of the body portion, in which the female port nozzle portion includes a communication port through which an inner portion of the female port nozzle portion is communicated with the inner cavity of the body portion on a proximal end of the female port nozzle portion, the body portion includes a distal end wall surface that extends radially outward from the communication port of the female port nozzle portion and faces the inner cavity, and a side wall surface that extends from an outer edge of the distal end wall surface in a proximal end direction and faces the inner cavity, the distal end wall surface of the body portion includes an inner edge portion adjacent to the communication port of the female port nozzle portion, and a concave portion arranged radially outside the inner edge portion and is concave in a distal end direction more than at least a part of the inner edge portion, a liquid lubricant is applied on the side wall surface of the body portion, and the concave portion of the distal end wall surface is arranged to fully surround the communication port of the female port nozzle portion and configured to store the liquid lubricant.

According to such a configuration, when the syringe is set up such that the distal end of the female port nozzle portion faces downward, the liquid lubricant dripping from the inner peripheral surface to the distal end wall surface of the body portion may be stored in the concave portion, so that it is possible to suppress the liquid lubricant from adhering to the inner peripheral surface of the female port nozzle portion. As a result, it is possible to secure prevention of the connection strength of the luer taper connection from lowering and prevention of the liquid lubricant from transferring to the male port nozzle portion.

In the syringe described above, the concave portion may include a first concave portion adjacent to the inner edge portion, and a second concave portion arranged radially outside the first concave portion.

According to such a configuration, the liquid lubricant may be stored in the first concave portion and the second concave portion, so that it is possible to further suppress the liquid lubricant from adhering to the inner peripheral surface of the female port nozzle portion.

In the syringe described above, the distal end wall surface may include an inclined surface inclined in the proximal end direction from the vicinity of the outer edge of the distal end wall surface to the vicinity of the communication port of the female port nozzle portion, and the concave portion may be formed of an outer edge portion of the inclined surface.

According to such a configuration, since the concave portion is formed of the inclined surface of the distal end wall surface, a configuration of the syringe may be simplified.

In the syringe described above, each of the first concave portion and the second concave portion may extend in a range smaller than 360° in a circumferential direction of the body portion, and the second concave portion may be arranged to cover an entire flat surface portion adjacent to the inner edge portion in which the first concave portion is not formed out of the distal end wall surface from radially outside.

In the syringe described above, each of a plurality of first concave portions and a plurality of second concave portions may be arranged at intervals in the circumferential direction of the body portion, and the second concave portions may be arranged to cover the flat surface portion located between the first concave portions adjacent to each other from radially outside.

In the syringe described above, it is possible that the liquid lubricant is not substantially applied on an inner peripheral surface of the female port nozzle portion.

According to such a configuration, it is possible to further secure prevention of the connection strength of the luer taper connection from lowering and prevention of the liquid lubricant from transferring to the male port nozzle portion.

A syringe assembly according to the present disclosure is provided with the syringe described above, and a gasket arranged in the body portion of the syringe and slidable on the side wall surface of the body portion, in which the distal end wall surface of the body portion includes an outer edge portion between the concave portion and the outer edge, and the gasket includes a distal end face capable of abutting the outer edge portion of the distal end wall surface.

According to such a configuration, when the gasket is displaced in the distal end direction with respect to the body portion such that the drug solution is allowed to flow out of the syringe, it becomes possible to reduce an amount of the drug solution remained between the distal end wall surface of the body portion and the distal end face of the gasket.

In the syringe assembly described above, the distal end face of the gasket may include a convex portion insertable into the concave portion of the distal end wall surface of the body portion.

According to such a configuration, when the gasket is displaced in the distal end direction with respect to the body portion such that the drug solution is allowed to flow out of the syringe, it becomes possible to reduce the amount of the drug solution remained between the distal end wall surface of the body portion and the distal end face of the gasket more.

In the syringe assembly described above, a portion facing the distal end wall surface out of the distal end face of the gasket may have a shape substantially the same as a shape of the distal end wall surface of the body portion.

According to such a configuration, when the gasket is displaced in the distal end direction with respect to the body portion such that the drug solution is allowed to flow out of the syringe, it becomes possible to further reduce the amount of the drug solution remained between the distal end wall surface of the body portion and the distal end face of the gasket.

In the syringe assembly described above, the distal end face of the gasket may be configured to abut the outer edge portion of the distal end wall surface of the body portion before abutting the inner edge portion of the distal end wall surface of the body portion when the gasket is displaced in the distal end direction with respect to the body portion.

According to such a configuration, when the gasket is displaced in the distal end direction with respect to the body portion such that the drug solution is allowed to flow out of the syringe, it becomes possible to still further reduce the amount of the drug solution remained between the distal end wall surface of the body portion and the distal end face of the gasket.

In accordance with another aspect, a syringe is disclosed comprising: a body portion including an inner; a female port nozzle portion that extends from a distal end of the body portion into which a male luer is inserted, the female port nozzle portion including a communication port through which an inner portion of the female port nozzle portion is communicated with the inner cavity of the body portion on a proximal end of the female port nozzle portion; a proximal end opening formed on a proximal end portion of the body portion, the body portion includes: a distal end wall surface that extends radially outward from the communication port of the female port nozzle portion and faces the inner cavity; and a side wall surface that extends from an outer edge of the distal end wall surface in a proximal end direction and faces the inner cavity; and the distal end wall surface of the body portion includes: an inner edge portion adjacent to the communication port of the female port nozzle portion; and a concave portion arranged radially outside the inner edge portion and is concave in a distal end direction more than at least a part of the inner edge portion, and wherein the concave portion of the distal end wall surface is arranged to fully surround the communication port of the female port nozzle portion.

A manufacturing method of a syringe according to the present disclosure is a manufacturing method of a syringe provided with a body portion including an inner cavity capable of being filled with a drug solution, a female port nozzle portion that extends from a distal end of the body portion into which a male luer is inserted, and a proximal end opening formed on a proximal end portion of the body portion, the method provided with preparing the syringe in which the female port nozzle portion includes a communication port through which an inner portion of the female port nozzle portion is communicated with the inner cavity of the body portion on a proximal end of the female port nozzle portion, the body portion includes a distal end wall surface that extends radially outward from the communication port of the female port nozzle portion and faces the inner cavity, and a side wall surface that extends from an outer edge of the distal end wall surface in a proximal end direction and faces the inner cavity, and the distal end wall surface of the body portion includes an inner edge portion adjacent to the communication port of the female port nozzle portion, and a concave portion arranged radially outside the inner edge portion to fully surround the communication port of the female port nozzle portion and is concave in a distal end direction more than at least a part of the inner edge portion, applying liquid lubricant on the side wall surface of the body portion, and holding the syringe in a state in which a distal end of the female port nozzle portion faces downward and storing a part of the liquid lubricant applied on the side wall surface of the body portion in the concave portion of the distal end wall surface.

According to such a method, it is possible to suppress the liquid lubricant from adhering to the inner peripheral surface of the female port nozzle portion, so that it is possible to secure the prevention of the connection strength of the luer taper connection from lowering and the prevention of the liquid lubricant from transferring to the male port nozzle portion.

In the manufacturing method of a syringe described above, it is possible that the liquid lubricant is stored in the concave portion of the distal end wall surface, so that the liquid lubricant is not substantially applied on an inner peripheral surface of the female port nozzle portion.

According to such a method, it is possible to further secure prevention of the connection strength of the luer taper connection from lowering and prevention of the liquid lubricant from transferring to the male port nozzle portion.

In the manufacturing method of a syringe described above, it is possible to prepare a storage container that stores the syringe, and hold the syringe in the storage container in a state in which the distal end of the female port nozzle portion faces downward.

According to such a method, the syringe is held in the storage container in a state in which the distal end of the female port nozzle portion faces downward, so that storage, conveyance and the like of the syringe may be efficiently performed. Furthermore, at that time, the liquid lubricant dripping from the side wall surface to the distal end wall surface of the body portion may be stored in the concave portion, so that it is possible to suppress the liquid lubricant from adhering to the inner peripheral surface of the female port nozzle portion.

According to the present disclosure, when the syringe is set up such that the distal end of the female port nozzle portion faces downward, the liquid lubricant dripping from the side wall surface to the distal end wall surface of the body portion may be stored in the concave portion of the distal end wall surface, so that it is possible to suppress the liquid lubricant from adhering to the inner peripheral surface of the female port nozzle portion. As a result, it is possible to secure prevention of the connection strength of the luer taper connection from lowering and prevention of the liquid lubricant from transferring to the male port nozzle portion.

BRIEF DESCRIPTION OF THE DRAWINGS

FIG. 2 is an enlarged cross-sectional view on a distal end side of the syringe assembly in FIG. 1.

FIG. 8A is a cross-sectional view of a storage container which stores a syringe with cap.

FIG. 8B is a cross-sectional view of a sterile bag which stores the storage container.

FIG. 9 is an explanatory view illustrating a state in which the liquid lubricant dripping from the side wall surface to the distal end wall surface of the body portion is stored in a concave portion.

FIG. 11 is an explanatory cross-sectional view of a concave portion and a convex portion according to a second example.

FIG. 13 is an explanatory cross-sectional view of a concave portion and a convex portion according to a third example.

DETAILED DESCRIPTION

Set forth below with reference to the accompanying drawings is a detailed description of embodiments of a syringe, a syringe assembly, and a manufacturing method of a syringe and representing examples of the inventive syringe, syringe assembly and manufacturing method of the syringe disclosed here.

Figure 1:
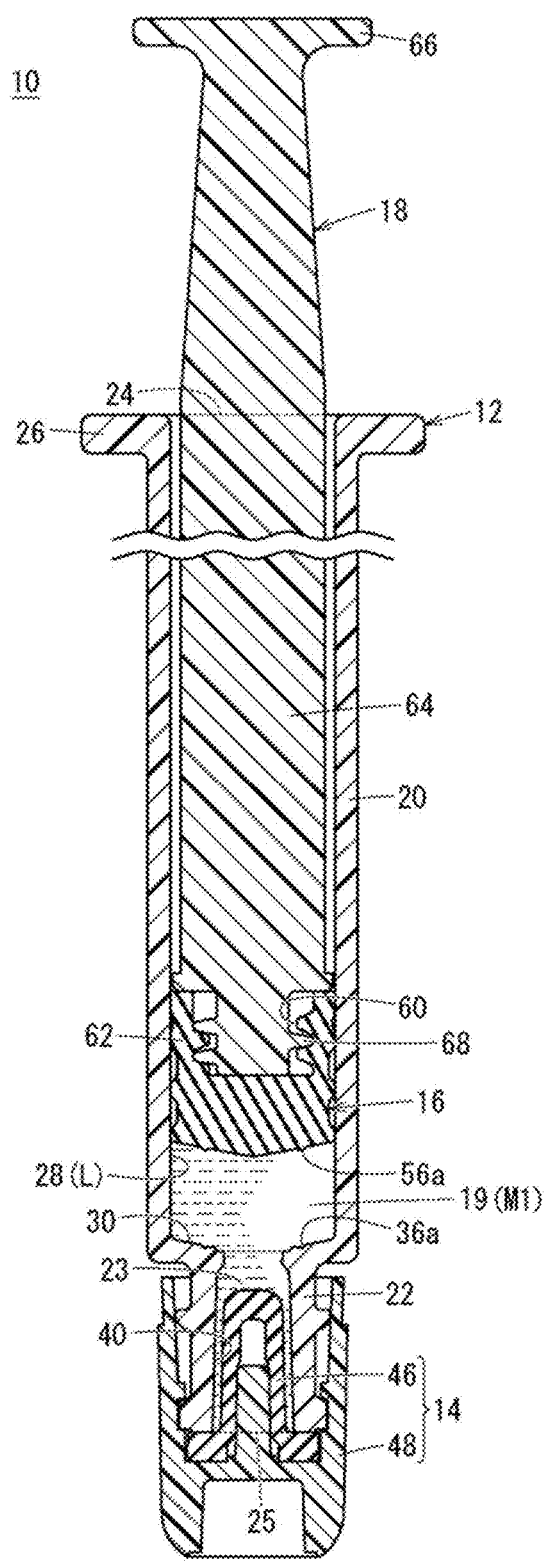
FIG. 1 is a longitudinal cross-sectional view of a syringe assembly according to an exemplary embodiment of the present disclosure.

As illustrated in FIG. 1, a syringe assembly 10 according to an exemplary embodiment of the present disclosure is provided with a syringe 12, a cap 14 attached to a distal end portion of the syringe 12, a gasket 16 inserted into the syringe 12 configured to be slidable in the syringe 12 in a liquid-tight manner, and a pusher 18 connected to the gasket 16. The syringe assembly 10 is configured as a prefilled syringe filled with a drug solution (i.e., medicine) M1 in advance.

In FIG. 1, the syringe 12 is provided with a body portion 20 including an inner cavity 19 capable of being filled with the drug solution M1, a female port nozzle portion 22 which extends from a distal end of the body portion 20 into which a male port nozzle portion 110 (refer to FIG. 5) being a male luer is inserted, a proximal end opening 24 formed on a proximal end portion of the body portion 20, and a distal end opening 25 formed on a distal end portion of the female port nozzle portion 22.

The body portion 20 is a hollow cylindrical portion into which the gasket 16 is slidably inserted. A flange 26 projecting radially outward is formed on an outer peripheral portion of the proximal end of the body portion 20. The body portion 20 includes a side wall surface 28 and a distal end wall surface 30.

The side wall surface 28 of the body portion 20 extends from an outer edge of the distal end wall surface 30 in a proximal end direction and faces the inner cavity 19 of the body portion 20. On the side wall surface 28 of the body portion 20, a liquid lubricant L is applied substantially uniformly in order to improve slidability of the gasket 16. As the liquid lubricant L, for example, silicone oil may be used. However, the liquid lubricant L is not limited to the silicone oil, and various types may also be used.

Figure 3A:
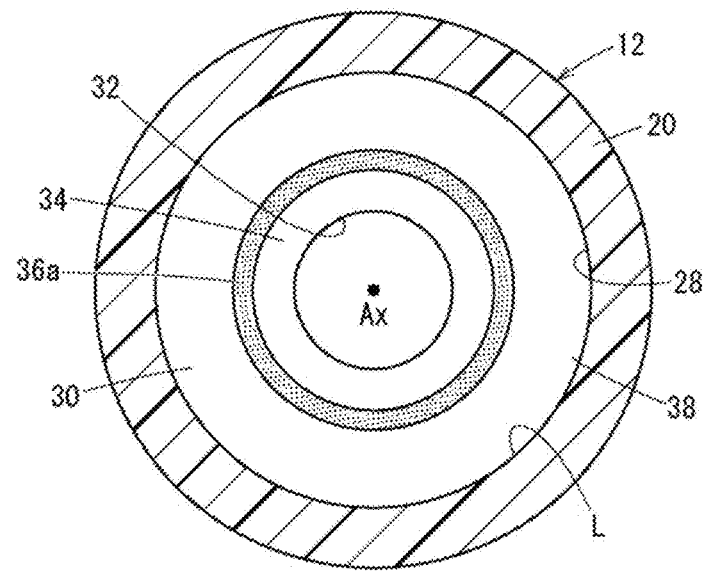
FIG. 3A is a cross-sectional view taken along line IIIA-IIIA in FIG. 2.

As illustrated in FIGS. 2 and 3A, the distal end wall surface 30 of the body portion 20 extends from a communication port 32 provided on a proximal end of the female port nozzle portion 22 radially outward and faces the inner cavity 19 of the body portion 20. The distal end wall surface 30 includes an inner edge portion 34 adjacent to the communication port 32 of the female port nozzle portion 22, a concave portion 36a arranged radially outside the inner edge portion 34 and is concave in a distal end direction from at least a part of the inner edge portion 34 (for example, a site located in a radially outermost portion of the inner edge portion 34), and an outer edge portion 38 between the concave portion 36a and the outer edge. The distal end wall surface 30 is inclined from the outer edge to the inner edge portion 34 in the distal end direction.

The concave portion 36a is arranged to fully surround the communication port 32 of the female port nozzle portion 22 and is able to store the liquid lubricant L. In accordance with an exemplary embodiment, the concave portion 36a is an annular groove extending 360° in a circumferential direction of the body portion 20 (refer to FIG. 3A). The concave portion 36a includes an inner surface a cross-section of which is circular (refer to FIG. 2). In this exemplary embodiment, an interval (i.e., distance) between the communication port 32 and the concave portion 36a is shorter than an interval (i.e., distance) between the outer edge of the distal end wall surface 30 and the concave portion 36a. However, a position in which the concave portion 36a is provided with respect to the distal end wall surface 30 may be set as desired.

In accordance with an exemplary embodiment, a size (depth dimension and width dimension) of the concave portion 36a can be determined according to an amount of the liquid lubricant L applied to the side wall surface 28 of the body portion 20. For example, the size of the concave portion 36a may be set such that a larger amount of liquid lubricant L than the amount of the liquid lubricant L applied to the side wall surface 28 of the body portion 20 may be stored (for example, 10 times the applied amount or more). However, the size of the concave portion 36a may be set as desired.

In FIG. 2, the female port nozzle portion 22 includes the communication port 32 with which an inner portion 23 of the female port nozzle portion 22 and the inner cavity 19 of the body portion 20 are communicated with each other on the proximal end of the female port nozzle portion 22. The female port nozzle portion 22 includes an inner peripheral surface 40 which may come into contact with an outer peripheral surface 116 (refer to FIG. 5) of the male port nozzle portion 110. The inner peripheral surface 40 is formed such that an inner diameter increases in the distal end direction. In accordance with an exemplary embodiment, the liquid lubricant L is not substantially applied to the inner peripheral surface 40 of the female port nozzle portion 22.

A fixing unit 42 which attachably/detachably fixes the cap 14 is provided on an outer peripheral surface of the distal end portion of the female port nozzle portion 22. In this exemplary embodiment, the fixing unit 42 is formed of two engaging projections 44 projecting in opposite directions across an axis line Ax of the syringe 12 and screwable into the cap 14.

The material of the syringe 12 can be, for example, various resins such as polypropylene, polyethylene, polystyrene, polyamide, polycarbonate, polyvinyl chloride, poly-(4-methylpentene-1), acrylic resin, acrylonitrile-butadiene-styrene copolymer, polyester such as polyethylene terephthalate, cyclic olefin polymer, and cyclic olefin copolymer. Among the various resins, resins such as polypropylene, cyclic olefin polymer, and cyclic olefin copolymer are preferable because they are rather easy to mold and have a relatively high heat resistance.

The cap 14 includes a sealing member 46 formed of an elastic member, which seals the distal end opening 25 of the syringe 12, and a tubular main body portion 48, which supports the sealing member 46. A female screw 50 is provided on an inner peripheral portion of the main body portion 48 and configured to screw into the fixing unit 42 (engaging projections 44) provided on the female port nozzle portion 22. In a state before use in which the cap 14 is attached to the female port nozzle portion 22, the distal end opening 25 is liquid-tightly sealed by the cap 14, so that the drug solution M1 does not leak from the distal end opening 25.

Figure 3B:
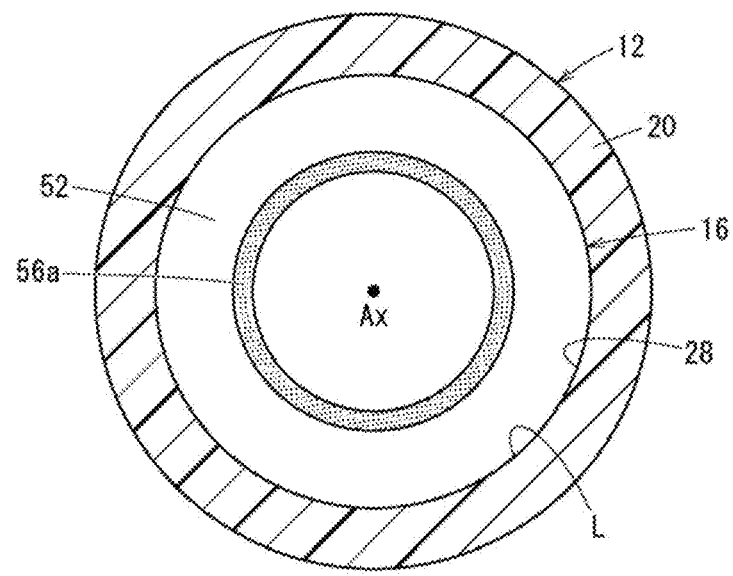
FIG. 3B is a cross-sectional view taken along line IIIB-IIIB in FIG. 2.

As illustrated in FIGS. 2 and 3B, the gasket 16 is arranged in the body portion 20 of the syringe 12 and is slidable on the side wall surface 28 of the body portion 20. The gasket 16 includes a distal end face 52 capable of abutting the outer edge portion 38 of the distal end wall surface 30 and an outer peripheral surface 54 which extends from an outer edge of the distal end face 52 in the proximal end direction. The distal end face 52 is directed in the distal end direction of the syringe 12 and pushes the drug solution M1 filled in the inner cavity 19 of the body portion 20 in the distal end direction.

A portion facing the distal end wall surface 30 out of the distal end face 52 of the gasket 16 has a shape substantially the same as that of the distal end wall surface 30 of the body portion 20. In accordance with an exemplary embodiment, for example, the distal end face 52 is inclined in the distal end direction from the outer edge of the distal end face 52 toward the center. For example, in a longitudinal cross-section of the syringe assembly 10 illustrated in FIG. 2, an inclination angle θ1 of the distal end face 52 with respect to the axis line Ax of the syringe 12 is slightly larger than an inclination angle θ2 of the distal end wall surface 30 with respect to the axis line Ax of the syringe 12.

As a result, when the gasket 16 is displaced in the distal end direction with respect to the body portion 20, the distal end face 52 of the gasket 16 abuts the outer edge portion 38 of the distal end wall surface 30 of the body portion 20 before abutting the inner edge portion 34 of the distal end wall surface 30 of the body portion 20. In accordance with another exemplary embodiment, the inclination angle θ1 of the distal end face 52 with respect to the axis line Ax of the syringe 12 may be the same as the inclination angle θ2 of the distal end wall surface 30 with respect to the axis line Ax of the syringe 12.

In FIGS. 2 and 3B, the distal end face 52 of the gasket 16 includes a convex portion 56a insertable into the concave portion 36a of the distal end wall surface 30 of the body portion 20. The convex portion 56a has a shape corresponding to the concave portion 36a of the distal end wall surface 30. In accordance with an exemplary embodiment, for example, the convex portion 56a includes an outer surface a cross-section of which is circular (refer to FIG. 2). The convex portion 56a is an annular projection extending 360° in the circumferential direction of the body portion 20 (refer to FIG. 3B).

In FIG. 2, a plurality of ring-shaped seal projections 58 is formed on the outer peripheral surface 54 of the gasket 16 at intervals in an axial direction. In a state in which the gasket 16 is inserted into the body portion 20, the seal projection 58 closely adheres to the side wall surface 28 of the body portion 20. As a result, the gasket 16 is slidable in the axial direction in the body portion 20 in a liquid-tight manner. As illustrated in FIG. 1, the gasket 16 is provided with a fitting concave portion 62 opening on the proximal end side with a female screw 60 formed on an inner peripheral portion of the gasket 16.

The material of the gasket 16, may be, for example, various rubber materials such as natural rubber, butyl rubber, isoprene rubber, butadiene rubber, styrene-butadiene rubber, and silicone rubber, various thermoplastic elastomers such as a polyurethane type, a polyester type, a polyamide type, an olefin type, and a styrene type, a mixture of the various rubber materials and/or various thermoplastic elastomers, or the like.

The pusher 18 includes a shaft portion 64 inserted into the body portion 20 and extends by a predetermined length, and a pusher flange 66 provided on a proximal end of the shaft portion 64. A male screw 68 inserted into the fitting concave portion 62 to screw into the female screw 60 of the gasket 16 is formed on a distal end portion of the shaft portion 64. The material of the pusher 18 may be selected from the materials of the syringe 12 described above.

The drug solution (medicine) M1 may be any type such as a powder medicine, a freeze-dried medicine, a solid medicine, and a liquid medicine. Such drug solution M1 includes, for example, protein preparations, antitumor agents, vitamins (multivitamins), various amino acids, antithrombotic agents such as heparin, insulin, antibiotics, analgesics, cardiotonic agents, intravenous injection anesthetics, medical narcotics, anti-parkinsonian agents, ulcer treatment agents, corticosteroids, arrhythmic agents and the like.

Figure 4:
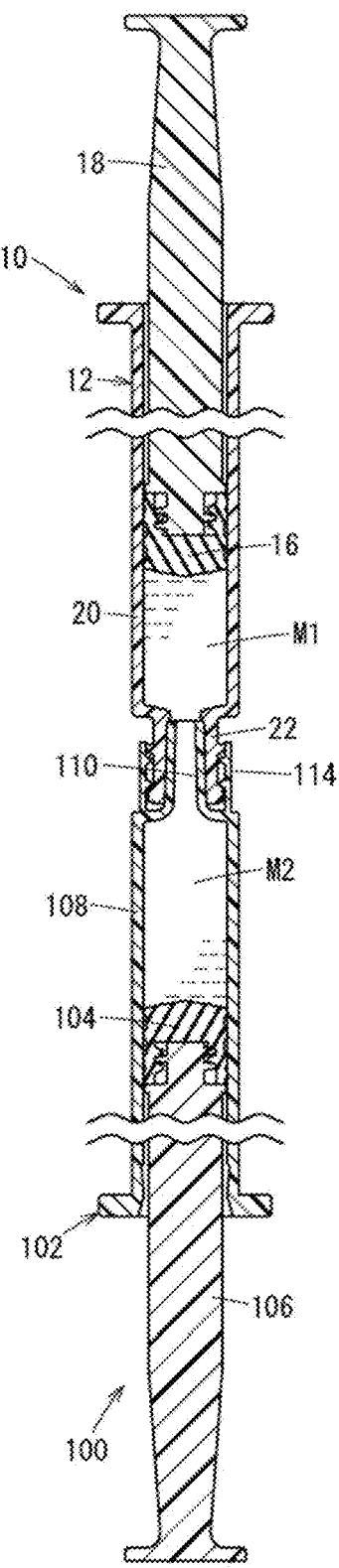
FIG. 4 is a first usage explanatory diagram of the syringe assembly in FIG. 1.

As illustrated in FIG. 4, when using the syringe assembly 10 described above, another syringe assembly 100 filled with a medical liquid M2 (dilution or dissolution liquid) is connected to this syringe assembly 10. The other syringe assembly 100 is provided with a syringe 102, a gasket 104, and a pusher 106.

Figure 5:
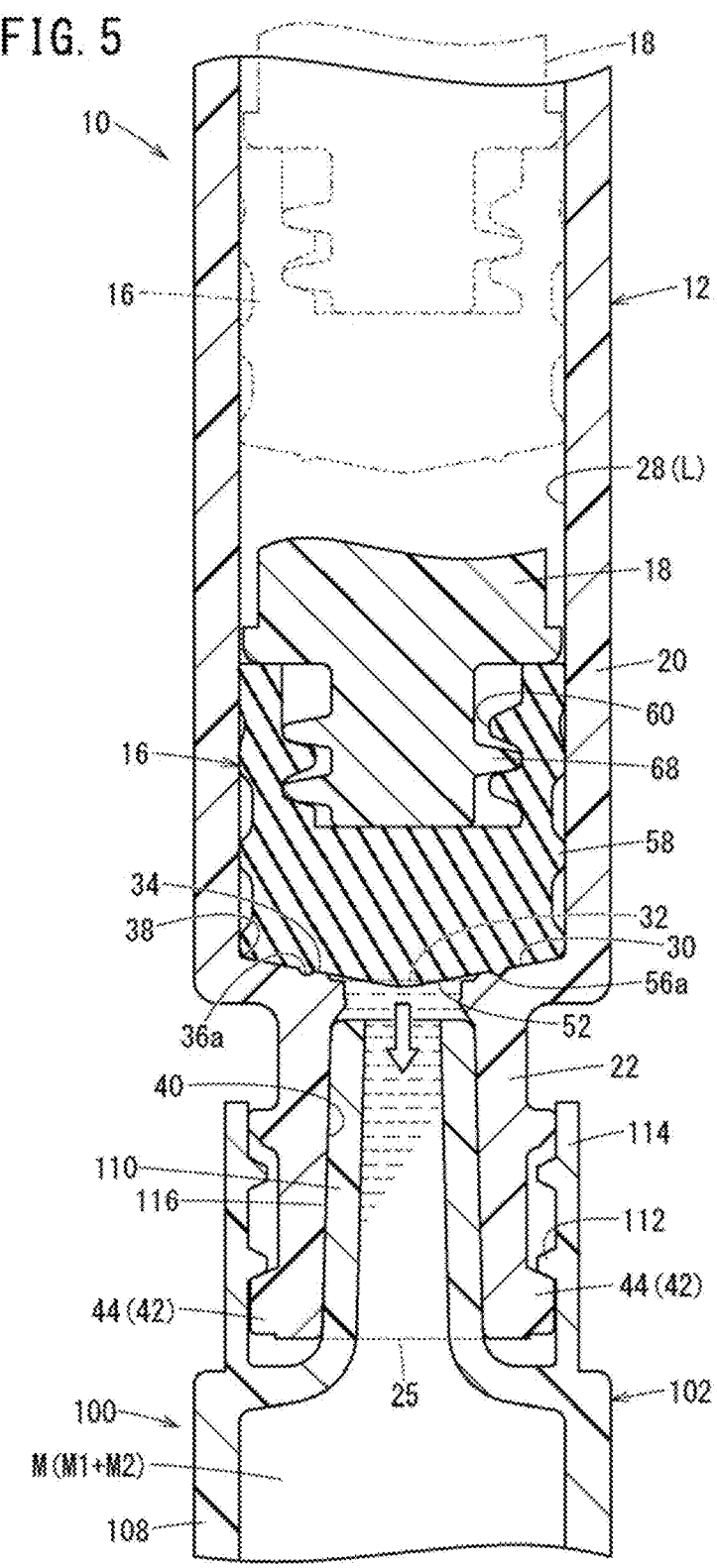
FIG. 5 is a second usage explanatory diagram of the syringe assembly in FIG. 1.

In FIG. 5, the syringe 102 includes a body portion 108, a male port nozzle portion 110 which extends from a distal end of the body portion 108 and is inserted into the female port nozzle portion 22, and a connecting unit 114 including a female screw 112 capable of engaging with the fixing unit 42 (engaging projections 44) of the female port nozzle portion 22 on an inner peripheral portion of the connecting unit 114. An outer peripheral surface 116 of the male port nozzle portion 110 is formed such that an outer diameter of the outer peripheral surface 116 of the male port nozzle portion 110 decreases in the distal end direction.

In a state in which the female port nozzle portion 22 (female luer) is connected to the male port nozzle portion 110 (male luer) (luer taper connection state), the inner peripheral surface 40 of the female port nozzle portion 22 is in contact with the outer peripheral surface 116 of the male port nozzle portion 110 in a liquid-tight manner. Therefore, leakage of the drug solution M1 and the medical liquid M2 from the syringe assemblies 10, 100 is prevented.

Then, in the luer taper connection state, the gasket 16 is displaced in the distal end direction with respect to the body portion 20 and the gasket 104 is displaced in the proximal end direction with respect to the body portion 108 to transfer the drug solution M1 in the syringe assembly 10 to the other syringe assembly 100 filled with the medical liquid M2, and the drug solution M1 and the medical liquid M2 are mixed in the other syringe assembly 100, so that a target drug solution M (M1+M2) may be dispensed. At that time, the distal end face 52 of the gasket 16 of the syringe assembly 10 comes into contact with the outer edge portion 38 of the distal end wall surface 30 and then comes into contact with the inner edge portion 34. Furthermore, at that time, the convex portion 56a of the gasket 16 is inserted into the concave portion 36a of the distal end wall surface 30.

Figure 6:
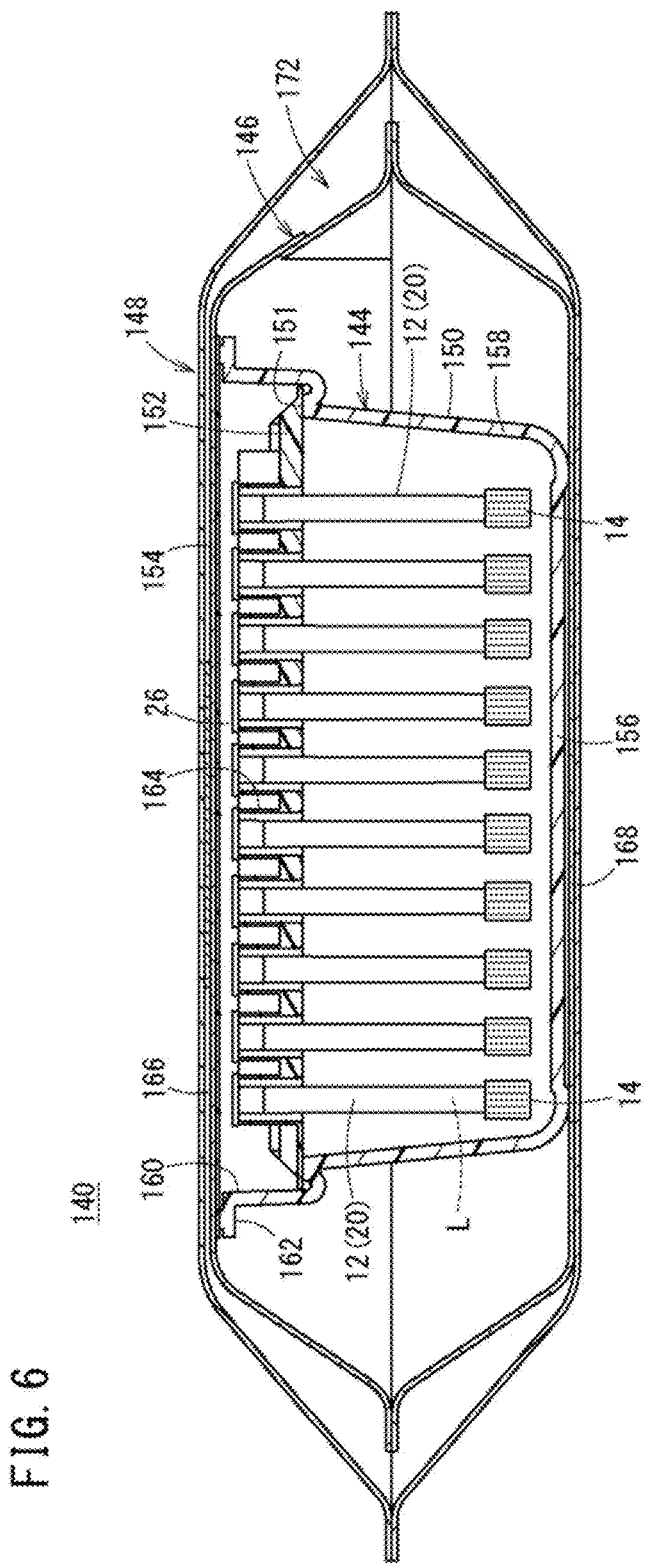
FIG. 6 is a cross-sectional view of a medical package.

A medical package 140 illustrated in FIG. 6 is provided with one or more syringes 12 with cap 14, a storage container 144 which stores the syringe 12 with cap 14, a sterile bag 146 which stores the storage container 144, and an outer package 148 which stores the sterile bag 146. Note that the syringe 12 is not filled with the drug solution M1 (refer to FIG. 1).

The storage container 144 includes a container main body 150 (tab), a holding member 152 (nest), and a sheet material 154. The container main body 150 is formed into a box shape including a bottom portion 156 forming a bottom wall, a side portion 158 forming a peripheral wall, and a flange portion 162 surrounding an opening 160 formed on an upper end portion of the side portion 158. The sheet material 154 is peelably fixed (joined) to an upper surface of the flange portion 162.

The holding member 152 is placed on a step 151 formed in the container main body 150 and holds a plurality of syringes 12 with cap 14 at the same height. The holding member 152 includes a plurality of hollow tubular projecting holding units 164. The flange 26 provided on the proximal end of the syringe 12 is hooked on an upper end of the projecting holding unit 164, so that the syringe 12 with cap 14 is held in a substantially perpendicularly suspended state.

The sheet material 154 is a lid member which seals the opening 160 of the container main body 150 and may be formed of a gas-permeable and bacteria-impermeable material. Therefore, the sheet material 154 may pass water vapor used as a sterilizing gas at the time of autoclave sterilization (high-pressure steam sterilization) in a manufacturing step of the medical package 140. Examples of a material of the sheet material 154 can include a plastic non-woven fabric, a plastic porous film and the like, for example. Examples of the plastic non-woven fabric can include non-woven polyolefin, for example.

The sterile bag 146 is a bag in which at least a part of the bag is gas permeable and bacteria impermeable. In this exemplary embodiment, the sterile bag 146 includes a first sheet 166 having gas permeability and bacteria impermeability and a second sheet 168 formed of gas-impermeable and bacteria-impermeable material (for example, polyethylene and the like), and peripheral edge portions of the first sheet 166 and the second sheet 168 are fused together.

In accordance with an exemplary embodiment, the outer package 148 is larger than the sterile bag 146. Accordingly, the sterile bag 146 in which the storage container 144 is stored, may be stored in the outer package 148. As described later, at the manufacturing step, after putting the sterile bag 146 in which the storage container 144 is stored into the outer package 148, an opening of the outer package 148 is sealed by a sealing device, so that the sterile bag 146 is externally packaged.

The medical package 140 configured in this manner is packed in a box to be shipped, and may be opened by, for example, a pharmaceutical manufacturer, and the syringe 12 with cap 14 is taken out. Then, the inner cavity 19 of the body portion 20 of the syringe 12 with cap 14 is filled with the drug solution M1, and the gasket 16 is inserted into the body portion 20 to complete the syringe assembly 10 illustrated in FIG. 1 (refer to FIG. 1).

Next, a manufacturing method of the syringe 12 according to this embodiment is described.

Figure 7C:
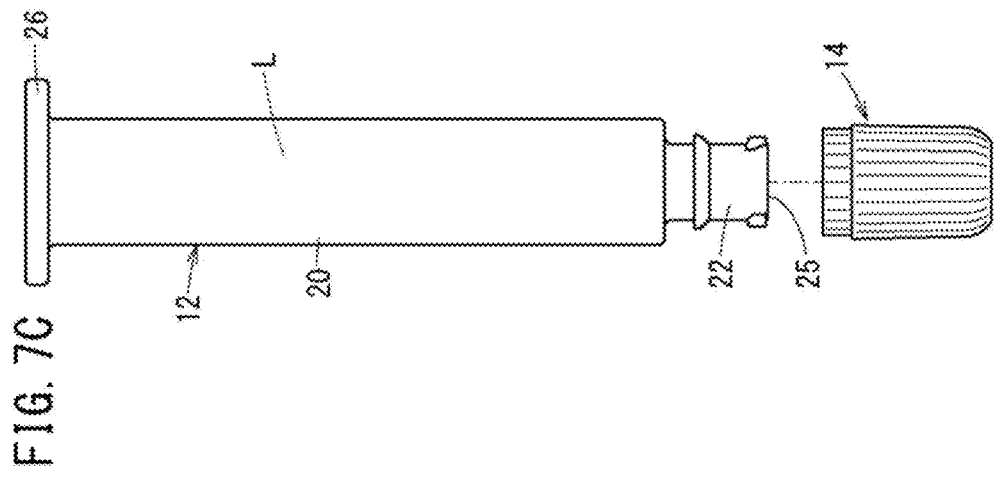
FIG. 7C is an explanatory diagram of a step of attaching a cap to the syringe.
Figure 7B:
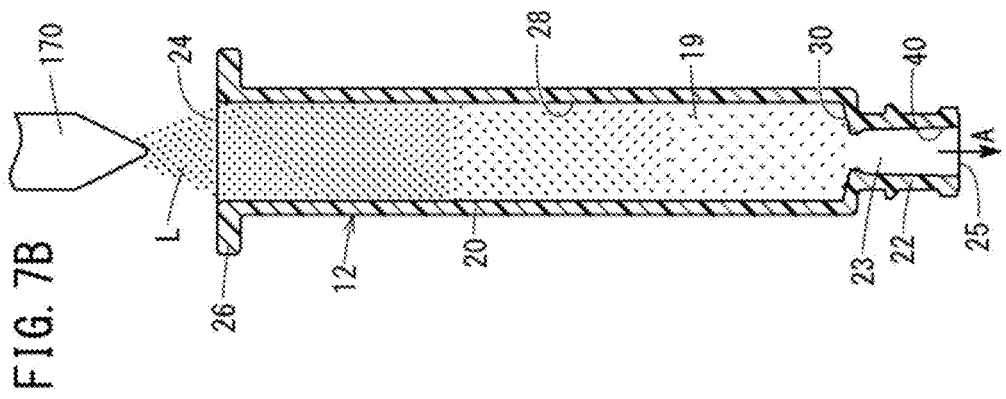
FIG. 7B is an explanatory diagram of a step of applying liquid lubricant to a side wall surface of the syringe.
Figure 7A:
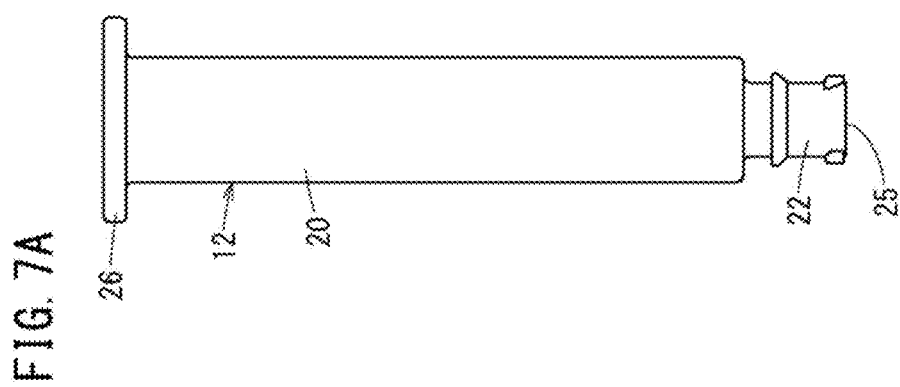
FIG. 7A is an explanatory diagram of a step of preparing the syringe.

As illustrated in FIG. 7A, the syringe 12 is prepared (syringe preparing step). The syringe 12 may be manufactured by injection molding, for example.

Next, as illustrated in FIG. 7B, the liquid lubricant L such as silicone oil is applied by spraying to the side wall surface 28 of the syringe 12 by a predetermined applying amount (applying step). Specifically, at the applying step, the syringe 12 is held with the proximal end opening 24 facing upward, and a spray nozzle 170 faces the proximal end opening 24. Then, the liquid lubricant L is discharged, for example, in a mist form from the spray nozzle 170 and sprayed to the side wall surface 28 of the syringe 12. As a result, the liquid lubricant L is applied to the side wall surface 28 of the syringe 12. In this exemplary embodiment, the liquid lubricant L is applied from the vicinity of the proximal end opening 24 to the vicinity of the distal end wall surface 30 of the syringe 12.

Furthermore, as illustrated in FIG. 7B, in this exemplary embodiment, when the liquid lubricant L is applied by spraying, air A is sucked from the female port nozzle portion 22 side. By spraying the liquid lubricant L while sucking air A from the female port nozzle portion 22 side in this manner, the liquid lubricant L may be applied to the vicinity of the distal end wall surface 30. Furthermore, it is possible to reduce spray unevenness and apply the liquid lubricant L more uniformly.

Next, as illustrated in FIG. 7C, the cap 14 is prepared, and the cap 14 is attached to the female port nozzle portion 22 of the syringe 12 to which the liquid lubricant L is applied to seal the distal end opening 25 of the syringe 12. However, the cap 14 may also be attached before the liquid lubricant L is applied.

Next, as illustrated in FIG. 8A, the storage container 144 described above is prepared (storage container preparing step), and one or more syringes 12 with cap 14 obtained in the above-described manner are stored in the container main body 150. Specifically, the syringe 12 with cap 14 is inserted into each projecting holding unit 164 of the holding member 152 with the distal end side facing downward, and a plurality of syringes 12 with cap 14 is suspended by the holding member 152, then the holding member 152 is placed in the container main body 150.

Next, the opening 160 of the container main body 150 is sealed with the sheet material 154. Specifically, the sheet material 154 is peelably fixed to the flange portion 162 of the container main body 150 to seal the opening 160 of the container main body 150. In this case, a fixing means, for example, fixing with an adhesive in addition to heat fusion. The opening 160 of the container main body 150 in which the syringe 12 with cap 14 is stored is sealed with the sheet material 154. As a result, as illustrated in FIG. 8A, the storage container 144 in which the syringe 12 with cap 14 not filled with the drug solution M1 is stored is obtained.

Next, as illustrated in FIG. 8B, a step of obtaining a package 172 is performed. In accordance with an exemplary embodiment, for example, first, the storage container 144 (the container main body 150 in which the syringe 12 with cap 14 is stored and the opening 160 is sealed with the sheet material 154) is packaged in the sterile bag 146. Specifically, after putting the storage container 144 in the sterile bag 146 an opening of which is opened, the opening of the sterile bag 146 is sealed. As a result, the opening 160 of the container main body 150 is sealed with the sheet material 154, the syringe 12 with cap 14 is stored in the storage container 144, and the package 172 obtained by storing the storage container 144 in the sterile bag 146 is obtained.

Next, the package 172 is sterilized. In this exemplary embodiment, autoclave sterilization may be performed as a sterilizing process. In the autoclave sterilization, water vapor which is a sterilizing gas permeates the sterile bag 146, so that the syringe 12 with cap 14 in the storage container 144 is sterilized.

After the sterilization of the package 172 is completed, next, the package 172 is put into the outer package 148 an opening of which is opened, and the opening of the outer package 148 is sealed to store the package 172 in the outer package 148. As a result, the medical package 140 illustrated in FIG. 6 is obtained.

In the medical package 140 obtained in this manner, as illustrated in FIG. 9, the liquid lubricant L applied to the side wall surface 28 of the body portion 20 of the syringe 12 might drip on the distal end wall surface 30. Then, the dripped liquid lubricant L is stored in the concave portion 36a provided on the distal end wall surface 30. Therefore, the liquid lubricant L is not substantially applied to the inner peripheral surface 40 of the female port nozzle portion 22.

The syringe 12, the syringe assembly 10, and the manufacturing method of the syringe 12 according to this exemplary embodiment may have the following features.

The distal end wall surface 30 of the body portion 20 of the syringe 12 includes the inner edge portion 34 adjacent to the communication port 32 of the female port nozzle portion 22, and the concave portion 36a arranged radially outside the inner edge portion 34 and is concave in the distal end direction more than at least a part of the inner edge portion 34. The liquid lubricant L is applied on the side wall surface 28 of the body portion 20. The concave portion 36a of the distal end wall surface 30 is arranged to fully surround the communication port 32 of the female port nozzle portion 22 and is able to store the liquid lubricant L.

As a result, when the syringe 12 is set up such that the distal end of the female port nozzle portion 22 faces downward, the liquid lubricant L dripping from the inner peripheral surface 40 to the distal end wall surface 30 of the body portion 20 may be stored in the concave portion 36a, so that it is possible to suppress the liquid lubricant L from adhering to the inner peripheral surface 40 of the female port nozzle portion 22. Therefore, it is possible to help secure prevention of connection strength of the luer taper connection from being lowered and the prevention of the liquid lubricant L from transferring to the male port nozzle portion 110.

In accordance with an exemplary embodiment, the liquid lubricant L is not substantially applied on the inner peripheral surface 40 of the female port nozzle portion 22. Therefore, it is possible to further help secure the prevention of the connection strength of the luer taper connection from lowering and the prevention of the liquid lubricant L from transferring to the male port nozzle portion 110.

The syringe assembly 10 is provided with the gasket 16 arranged in the body portion 20 of the syringe 12 and is slidable on the side wall surface 28 of the body portion 20. The distal end wall surface 30 of the body portion 20 includes the outer edge portion 38 between the concave portion 36a and the outer edge, and the gasket 16 includes the distal end face 52 capable of abutting the outer edge portion 38 of the distal end wall surface 30.

As a result, when the gasket 16 is displaced in the distal end direction with respect to the body portion 20 such that the drug solution M1 is allowed to flow out of the syringe 12, it becomes possible to reduce the amount of the drug solution M1 remaining between the distal end wall surface 30 of the body portion 20 and the distal end face 52 of the gasket 16.

The distal end face 52 of the gasket 16 includes the convex portion 56a insertable into the concave portion 36a of the distal end wall surface 30 of the body portion 20. As a result, when the gasket 16 is displaced in the distal end direction with respect to the body portion 20 such that the drug solution M1 is allowed to flow out of the syringe 12, it becomes possible to further reduce the amount of the drug solution M1 remaining between the distal end wall surface 30 and the distal end face 52 of the gasket 16.

A portion facing the distal end wall surface 30 out of the distal end face 52 of the gasket 16 has a shape substantially the same as that of the distal end wall surface 30 of the body portion 20. As a result, when the gasket 16 is displaced in the distal end direction with respect to the body portion 20 such that the drug solution M1 is allowed to flow out of the syringe 12, it becomes possible to further reduce the amount of the drug solution M1 remaining between the distal end wall surface 30 and the distal end face 52 of the gasket 16.

The distal end face 52 of the gasket 16 is configured to abut the outer edge portion 38 of the distal end wall surface 30 of the body portion 20 before abutting the inner edge portion 34 of the distal end wall surface 30 of the body portion 20 when the gasket 16 is displaced in the distal end direction with respect to the body portion 20. As a result, when the gasket 16 is displaced in the distal end direction with respect to the body portion 20 such that the drug solution M1 is allowed to flow out of the syringe 12, it becomes possible to still further reduce the amount of the drug solution M1 remaining between the distal end wall surface 30 and the distal end face 52 of the gasket 16.

In the manufacturing method of the syringe 12, the syringe 12 including the concave portion 36a on the distal end wall surface 30 is prepared, the liquid lubricant L is applied on the side wall surface 28 of the body portion 20, and the syringe 12 is held in a state in which the distal end of the female port nozzle portion 22 faces downward to store a part of the liquid lubricant L in the concave portion 36a of the distal end wall surface 30. Therefore, it is possible to suppress the liquid lubricant L from adhering to the inner peripheral surface 40 of the female port nozzle portion 22, so that it is possible to secure the prevention of the connection strength of the luer taper connection from lowering and the prevention of the liquid lubricant L from transferring to the male port nozzle portion 110.

In the manufacturing method of the syringe 12, by storing the liquid lubricant L in the concave portion 36a of the distal end wall surface 30, the liquid lubricant L is not substantially applied on the inner peripheral surface 40 of the female port nozzle portion 22. Therefore, it is possible to further help secure the prevention of the connection strength of the luer taper connection from lowering and the prevention of the liquid lubricant L from transferring to the male port nozzle portion 110.

In the manufacturing method of the syringe 12, the storage container 144 which stores the syringe 12 is prepared, and the syringe 12 is held in the storage container 144 in a state in which the distal end of the female port nozzle portion 22 faces downward. As a result, storage, conveyance and the like of the syringe 12 may be efficiently performed. Furthermore, at that time, the liquid lubricant L dripping from the side wall surface 28 to the distal end wall surface 30 of the body portion 20 may be stored in the concave portion 36a, so that it is possible to suppress the liquid lubricant L from adhering to the inner peripheral surface 40 of the female port nozzle.

Next, concave portions 36b to 36f and convex portions 56b to 56f according to first to fifth examples of the syringe assembly 10 are described. Note that, the concave portions 36b to 36f are provided on the distal end wall surface 30 of the syringe 12, and the convex portions 56b to 56f are provided on the distal end face 52 of the gasket 16.

Figure 10:
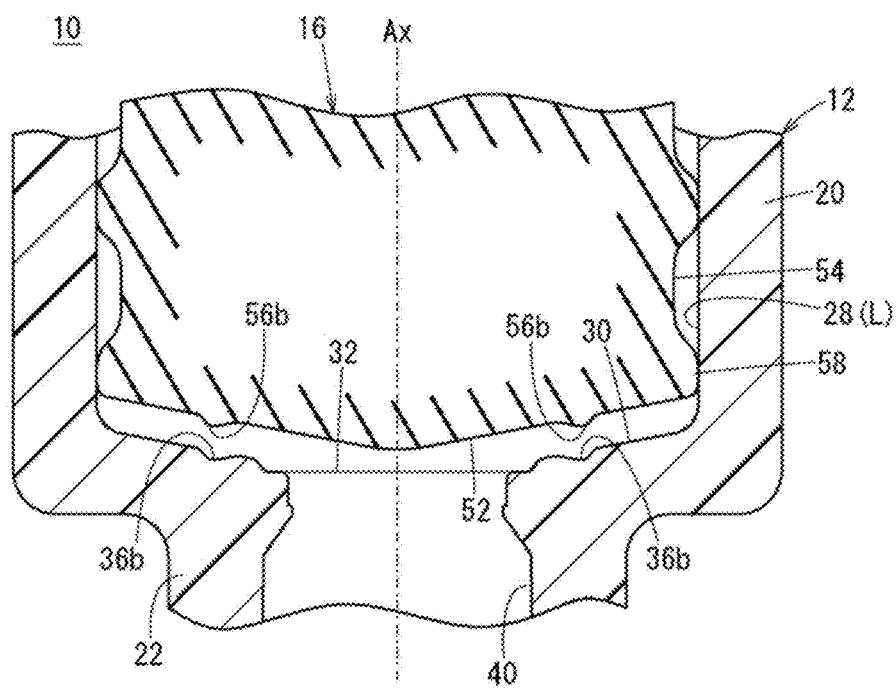
FIG. 10 is an explanatory cross-sectional view of a concave portion and a convex portion according to a first example.

The concave portion 36b and the convex portion 56b according to the first example are described with reference to FIG. 10. As illustrated in FIG. 10, the concave portion 36b has a triangular cross-section. The shape of the concave portion 36b other than the cross-section is the same as that of the concave portion 36a described above. Furthermore, the convex portion 56b is formed to have a triangular cross-section (shape corresponding to the concave portion 36b). The shape of the convex portion 56b other than the cross-section is the same as that of the above-described convex portion 56a. According to such concave portion 36b and convex portion 56b, the effects similar to those of the concave portion 36a and the convex portion 56a described above may be obtained.

Figure 12A:
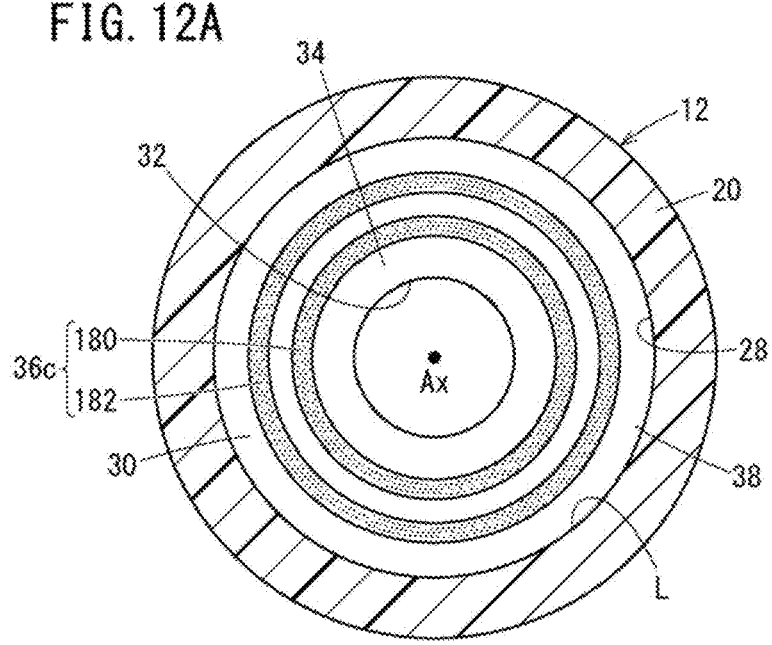
FIG. 12A is a cross-sectional view taken along line XIIA-XIIA in FIG. 11.

The concave portion 36c and the convex portion 56c according to the second example are described with reference to FIGS. 11 to 12B. As illustrated in FIGS. 11 and 12A, the concave portion 36c includes a first concave portion 180 adjacent to the inner edge portion 34 and a second concave portion 182 arranged radially outside of the first concave portion 180. The first concave portion 180 is concave in the distal end direction more than at least a part of the inner edge portion 34. A cross-sectional shape of each of the first concave portion 180 and the second concave portion 182 is the same as the cross-sectional shape of the concave portion 36a described above. The first concave portion 180 and the second concave portion 182 are annular grooves extending 360° in the circumferential direction of the body portion 20.

Figure 12B:
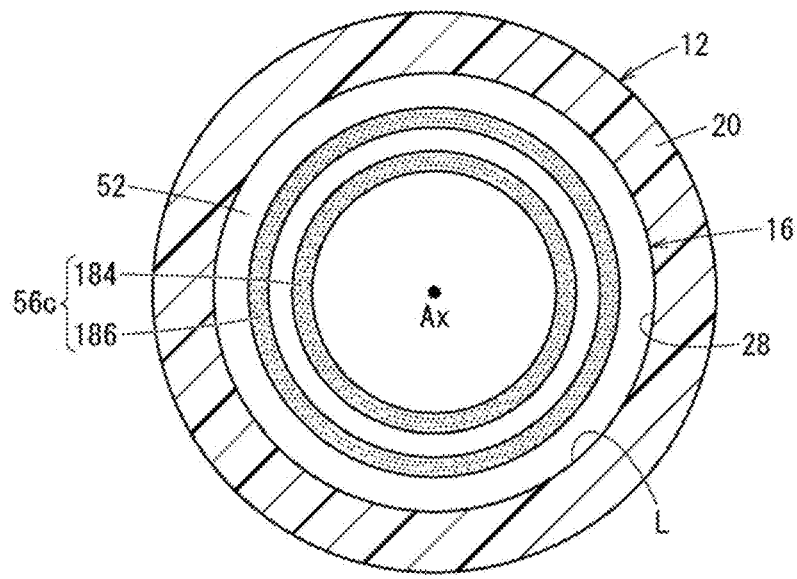
FIG. 12B is a cross-sectional view taken along line XIIB-XIIB in FIG. 11.

As illustrated in FIGS. 11 and 12B, the convex portion 56c includes a first convex portion 184 insertable into the first concave portion 180 and a second convex portion 186 insertable into the second concave portion 182. The second convex portion 186 is arranged radially outside the first convex portion 184. A cross-sectional shape of each of the first convex portion 184 and the second convex portion 186 is the same as the cross-sectional shape of the convex portion 56a described above. The first convex portion 184 and the second convex portion 186 are annular projections extending 360° in the circumferential direction of the body portion 20.

In this case, the liquid lubricant L may be stored in the first concave portion 180 and the second concave portion 182, so that it is possible to further suppress the liquid lubricant L from adhering to the inner peripheral surface 40 of the female port nozzle portion 22.

The concave portion 36d and the convex portion 56d according to the third example are described with reference to FIG. 13. As illustrated in FIG. 13, the distal end wall surface 30 includes an inclined surface 188 inclined in the proximal end direction from the vicinity of the outer edge of the distal end wall surface 30 to the vicinity of the communication port 32 of the female port nozzle portion 22, and the concave portion 36d is formed of an outer edge portion of the inclined surface 188. The concave portion 36d is concave in the distal end direction more than at least a part of the inner edge portion 34. The inclined surface 188 is inclined with respect to a plane orthogonal to the axis line Ax of the syringe 12. The concave portion 36d extends into an annular shape. Note that an annular convex portion 190 is formed on a proximal end portion of the inner peripheral surface 40 of the female port nozzle portion 22.

The distal end face 52 of the gasket 16 includes a central convex portion 192 capable of abutting the annular convex portion 190 and an inclined surface 194 inclined in the proximal end direction from the vicinity of the outer edge of the distal end face 52 to the vicinity of the central convex portion 192, and the convex portion 56d is formed of an outer edge portion of the inclined surface 194. The inclined surface 194 is substantially parallel to the inclined surface 188. The convex portion 56d has a shape corresponding to the concave portion 36d.

In accordance with an exemplary embodiment, since the concave portion 36d is formed of the inclined surface 188 of the distal end wall surface 30, a configuration of the syringe 12 may be simplified.

Figure 14A:
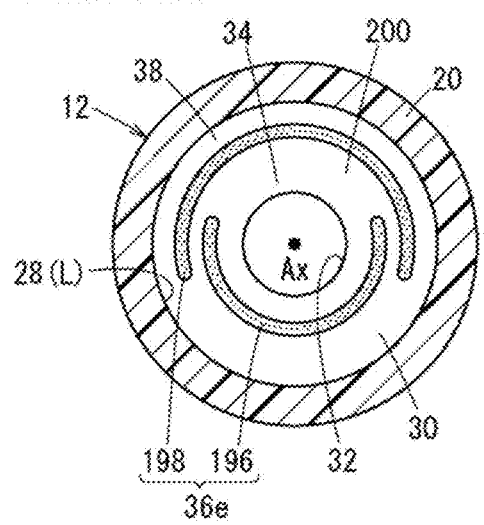
FIG. 14A is an explanatory cross-sectional view of a concave portion according to a fourth example.

The concave portion 36e and the convex portion 56e according to the fourth example are described with reference to FIGS. 14A and 14B. As illustrated in FIG. 14A, the concave portion 36e includes a first concave portion 196 adjacent to the inner edge portion 34 and a second concave portion 198 arranged radially outside the first concave portion 196. The first concave portion 196 extends in a range smaller than 360° in the circumferential direction of the body portion 20. Specifically, the first concave portion 196 extends into a semi-circular shape over a range of about 180° in the circumferential direction of the body portion 20. The first concave portion 196 is concave in the distal end direction more than at least a part of the inner edge portion 34.

The second concave portion 198 is arranged to cover an entire flat surface portion 200 adjacent to the inner edge portion 34 in which the first concave portion 196 is not formed out of the distal end wall surface 30 from radially outside. Specifically, the second concave portion 198 extends 180° or more in the circumferential direction of the body portion 20. In accordance with an exemplary embodiment, for example, the second concave portion 198 extends in the circumferential direction of the body portion 20 such that both ends of the second concave portion 198 are located radially outside the first concave portion 196. A cross-sectional shape of each of the first concave portion 196 and the second concave portion 198 may be set as desired, and may be formed, for example, into the same shape as the cross-sectional shape of the concave portion 36a or the concave portion 36b described above.

Figure 14B:
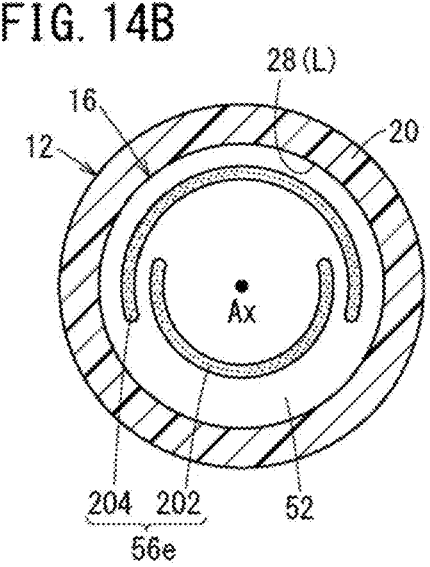
FIG. 14B is an explanatory cross-sectional view of a convex portion according to the fourth example.

As illustrated in FIG. 14B, the convex portion 56e includes a first convex portion 202 insertable into the first concave portion 196 and a second convex portion 204 insertable into the second concave portion 198. The first convex portion 202 is arranged in a position facing the first concave portion 196, and the second convex portion 204 is arranged in a position facing the second concave portion 198. Cross-sectional shapes of the first convex portion 202 and the second convex portion 204 are the same as the cross-sectional shapes of the first concave portion 196 and the second concave portion 198, respectively. According to such concave portion 36e and convex portion 56e, the effects similar to those of the concave portion 36a and the convex portion 56a described above may be obtained.

Figure 14C:
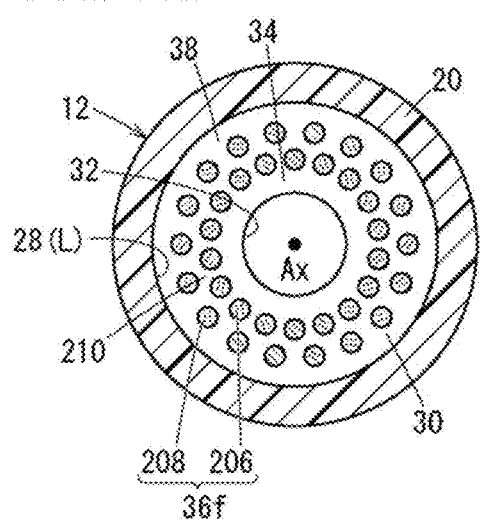
FIG. 14C is an explanatory cross-sectional view of a concave portion according to a fifth example.

The concave portion 36f and the convex portion 56f according to the fifth example are described with reference to FIGS. 14C and 14D. As illustrated in FIG. 14C, the concave portion 36f includes a plurality of first concave portions 206 adjacent to the inner edge portion 34 and a plurality of second concave portions 208 arranged radially outside the first concave portions 206. The plurality of first concave portions 206 is arranged at intervals in the circumferential direction of the body portion 20. The first concave portion 206 is formed into a circular shape in planar view. However, the first concave portion 206 may also be formed, for example, into a desired shape such as an elliptical shape or a polygonal shape in planar view. The first concave portion 206 is concave in the distal end direction more than at least a part of the inner edge portion 34.

The plurality of second concave portions 208 is arranged at intervals in the circumferential direction of the body portion 20. The plurality of second concave portions 208 is arranged to cover a flat surface portion 210 located between the adjacent first concave portions 206 from radially outside and located radially outside the first concave portions 206 located on both sides of the flat surface portion 210. The second concave portion 208 may be formed, for example, into a desired shape such as an elliptical shape or a polygonal shape in planar view. The first concave portion 206 and the second concave portion 208 may be rather easily formed by, for example, embossing the distal end wall surface 30 of the body portion 20.

Figure 14D:
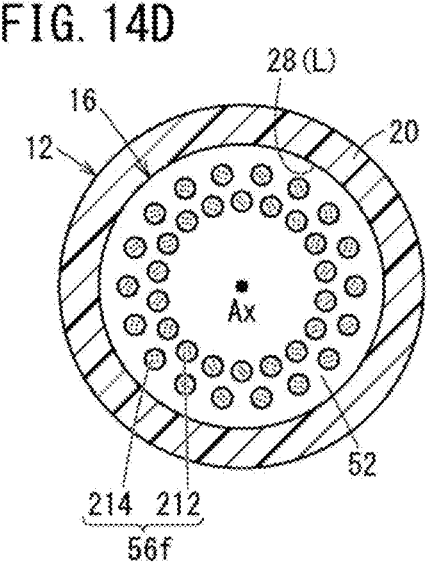
FIG. 14D is an explanatory cross-sectional view of a convex portion according to the fifth example.

As illustrated in FIG. 14D, the convex portion 56f includes a plurality of first convex portions 212 insertable into a plurality of first concave portions 206 and a plurality of second convex portions 214 insertable into a plurality of second concave portions 208. The first convex portion 212 is provided in a position facing the first concave portion 206, and the second convex portion 214 is provided in a position facing the second concave portion 208. Cross-sectional shapes of the first convex portion 212 and the second convex portion 214 are the same as the cross-sectional shapes of the first concave portion 206 and the second concave portion 208, respectively. According to such concave portion 36f and convex portion 56f, effects similar to those of the concave portion 36a and the convex portion 56a described above may be obtained.

In accordance with an exemplary embodiment, in the syringe assembly 10, the convex portions 56a to 56f of the gasket 16 may be omitted.

The syringe, the syringe assembly, and the manufacturing method of the syringe according to the present disclosure are not limited to the above-described embodiments, and various configurations may be adopted without departing from the gist of the present disclosure.

The detailed description above describes embodiments of a syringe, a syringe assembly, and a manufacturing method of a syringe. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:
1. A syringe comprising:
 a body portion including an inner cavity configured to be filled with a drug solution;
 a female port nozzle portion that extends from a distal end of the body portion into which a male luer is inserted;
 a proximal end opening formed on a proximal end portion of the body portion;
 the female port nozzle portion including a communication port through which an inner portion of the female port nozzle portion is communicated with the inner cavity of the body portion on a proximal end of the female port nozzle portion; and
 the body portion includes:
  a distal end wall surface that extends radially outward from the communication port of the female port nozzle portion and faces the inner cavity; and
  a side wall surface that extends from an outer edge of the distal end wall surface in a proximal end direction and faces the inner cavity;
 the distal end wall surface of the body portion includes:
  an inner edge portion adjacent to the communication port of the female port nozzle portion; and
  a concave portion in the distal end wall surface and arranged radially outside the inner edge portion and is concave in a distal end direction more than at least a part of the inner edge portion; and
 a liquid lubricant is applied on the side wall surface of the body portion, and wherein the concave portion of the distal end wall surface is arranged to fully surround the communication port of the female port nozzle portion and configured to store the liquid lubricant.
2. The syringe according to claim 1, wherein the concave portion comprises:
 a first concave portion adjacent to the inner edge portion; and
 a second concave portion arranged radially outside the first concave portion.

3. The syringe according to claim 2, comprising:
each of the first concave portion and the second concave portion extending in a range smaller than 360° in a circumferential direction of the body portion, and wherein the second concave portion is arranged to cover an entire flat surface portion adjacent to the inner edge portion in which the first concave portion is not formed out of the distal end wall surface from radially outside.

4. The syringe according to claim 3, comprising:
each of a plurality of first concave portions and a plurality of second concave portions being arranged at intervals in the circumferential direction of the body portion, and wherein the second concave portions are arranged to cover the flat surface portion located between the first concave portions adjacent to each other from radially outside.

5. The syringe according to claim 1, wherein the distal end wall surface includes an inclined surface inclined in the proximal end direction from the vicinity of the outer edge of the distal end wall surface to the vicinity of the communication port of the female port nozzle portion, and the concave portion is formed of an outer edge portion of the inclined surface.

6. The syringe according to claim 1, wherein the liquid lubricant is applied on an inner peripheral surface of the female port nozzle portion.

7. A syringe assembly comprising:
the syringe according to claim 1; and
a gasket arranged in the body portion of the syringe and slidable on the side wall surface of the body portion;
wherein the distal end wall surface of the body portion includes an outer edge portion between the concave portion and the outer edge; and
the gasket includes a distal end face capable of abutting the outer edge portion of the distal end wall surface.

8. The syringe assembly according to claim 7, wherein the distal end face of the gasket includes a convex portion insertable into the concave portion of the distal end wall surface of the body portion.

9. The syringe assembly according to claim 8, wherein a portion facing the distal end wall surface out of the distal end face of the gasket has a shape substantially the same as a shape of the distal end wall surface of the body portion.

10. The syringe assembly according claim 7, wherein the distal end face of the gasket is configured to abut the outer edge portion of the distal end wall surface of the body portion before abutting the inner edge portion of the distal end wall surface of the body portion when the gasket is displaced in the distal end direction with respect to the body portion.

11. A syringe comprising:
a body portion including an inner;
a female port nozzle portion that extends from a distal end of the body portion into which a male luer is inserted, the female port nozzle portion including a communication port through which an inner portion of the female port nozzle portion is communicated with the inner cavity of the body portion on a proximal end of the female port nozzle portion;
a proximal end opening formed on a proximal end portion of the body portion, the body portion includes:
a distal end wall surface that extends radially outward from the communication port of the female port nozzle portion and faces the inner cavity; and
a side wall surface that extends from an outer edge of the distal end wall surface in a proximal end direction and faces the inner cavity; and
the distal end wall surface of the body portion includes:
an inner edge portion adjacent to the communication port of the female port nozzle portion; and
a concave portion in the distal end wall surface and arranged radially outside the inner edge portion and is concave in a distal end direction more than at least a part of the inner edge portion, and wherein the concave portion of the distal end wall surface is arranged to fully surround the communication port of the female port nozzle portion.

12. The syringe according to claim 11, wherein the concave portion comprises:
a first concave portion adjacent to the inner edge portion; and
a second concave portion arranged radially outside the first concave portion.

13. The syringe according to claim 12, comprising:
each of the first concave portion and the second concave portion extending in a range smaller than 360° in a circumferential direction of the body portion, and wherein the second concave portion is arranged to cover an entire flat surface portion adjacent to the inner edge portion in which the first concave portion is not formed out of the distal end wall surface from radially outside.

14. The syringe according to claim 13, comprising:
each of a plurality of first concave portions and a plurality of second concave portions being arranged at intervals in the circumferential direction of the body portion, and wherein the second concave portions are arranged to cover the flat surface portion located between the first concave portions adjacent to each other from radially outside.

15. The syringe according to claim 11, wherein the distal end wall surface includes an inclined surface inclined in the proximal end direction from the outer edge of the distal end wall surface to the communication port of the female port nozzle portion, and the concave portion is formed of an outer edge portion of the inclined surface.

16. A syringe assembly comprising:
the syringe according to claim 11; and
a gasket arranged in the body portion of the syringe and slidable on the side wall surface of the body portion, the gasket including a distal end face configured to abut the outer edge portion of the distal end wall surface, and wherein the distal end wall surface of the body portion includes an outer edge portion between the concave portion and the outer edge.

17. The syringe assembly according to claim 16, wherein the distal end face of the gasket includes a convex portion configured to be inserted into the concave portion of the distal end wall surface of the body portion, and wherein a portion facing the distal end wall surface out of the distal end face of the gasket has a shape substantially the same as a shape of the distal end wall surface of the body portion.

18. A manufacturing method of a syringe provided with a body portion including an inner cavity capable of being filled with a drug solution, a female port nozzle portion that extends from a distal end of the body portion into which a male luer is inserted, and a proximal end opening formed on a proximal end portion of the body portion, the method comprising:
preparing the syringe in which the female port nozzle portion includes a communication port through which an inner portion of the female port nozzle portion is communicated with the inner cavity of the body portion on a proximal end of the female port nozzle portion, the body portion includes a distal end wall surface that extends radially outward from the communication port of the female port nozzle portion and faces the inner cavity, and a side wall surface that extends from an outer edge of the distal end wall surface in a proximal end direction and faces the inner cavity, and the distal end wall surface of the body portion includes an inner edge portion adjacent to the communication port of the female port nozzle portion, and a concave portion in the distal end wall surface and arranged radially outside the inner edge portion to fully surround the communication port of the female port nozzle portion and is concave in a distal end direction more than at least a part of the inner edge portion;

applying liquid lubricant on the side wall surface of the body portion; and holding the syringe in a state in which a distal end of the female port nozzle portion faces downward and storing a part of the liquid lubricant applied on the side wall surface of the body portion in the concave portion of the distal end wall surface.

19. The manufacturing method of a syringe according to claim 18, further comprising:

storing the liquid lubricant in the concave portion of the distal end wall surface.

20. The manufacturing method of a syringe according to claim 19, comprising:

preparing a storage container that stores the syringe; and holding the syringe in the storage container in a state in which the distal end of the female port nozzle portion faces downward.

* * * * *